(12) United States Patent
Ott

(10) Patent No.: US 7,654,952 B2
(45) Date of Patent: Feb. 2, 2010

(54) VIDEOLARYNGOSTROBOSCOPE

(76) Inventor: Ciro Timoteo Ott, Rua Maestro Herrmann, 343 82100-360 - Curitiba (BR)

( * ) Notice: Subject to any disclaimer, the term of this patent is extended or adjusted under 35 U.S.C. 154(b) by 391 days.

(21) Appl. No.: 11/382,613

(22) Filed: May 10, 2006

(65) Prior Publication Data

US 2007/0265504 A1    Nov. 15, 2007

(51) Int. Cl.
*A61B 1/06* (2006.01)
(52) U.S. Cl. .................... 600/178; 600/179; 600/199
(58) Field of Classification Search ................ 600/101, 600/109, 117, 118, 126, 160, 178, 179, 185, 600/186, 188, 189, 199, 200; 348/65, 68
See application file for complete search history.

(56) References Cited

U.S. PATENT DOCUMENTS

| | | | | |
|---|---|---|---|---|
| 3,026,449 | A * | 3/1962 | Rappaport | 315/166 |
| 5,894,369 | A * | 4/1999 | Akiba et al. | 359/820 |
| 6,734,893 | B1 * | 5/2004 | Hess et al. | 348/68 |
| 2002/0128535 | A1 * | 9/2002 | Kikuchi et al. | 600/101 |
| 2004/0095464 | A1 * | 5/2004 | Miyagi et al. | 348/65 |
| 2004/0215061 | A1 * | 10/2004 | Kimmel et al. | 600/179 |
| 2006/0079737 | A1 * | 4/2006 | Heaton et al. | 600/199 |
| 2007/0097702 | A1 * | 5/2007 | Crowder | 362/570 |

FOREIGN PATENT DOCUMENTS

| | | | |
|---|---|---|---|
| JP | 2000139832 A | * | 5/2000 |
| JP | 2000166867 A | * | 6/2000 |
| JP | 2002172088 A | * | 6/2002 |
| JP | 2002306410 A | * | 10/2002 |

* cited by examiner

*Primary Examiner*—John P Leubecker
*Assistant Examiner*—Samuel Candler
(74) *Attorney, Agent, or Firm*—Stephen M. Nipper; Dykas, Shaver & Nipper, LLP

(57) ABSTRACT

An innovative one-piece videolaryngostroboscope that provides slow motion visualization and detailed analysis of the vocal cords movements, which are imperceptible to the naked eye due, by means of a video camera with stroboscopic; said apparatus is used to perform examinations in patients, aiming to assess the incidence of larynx cancer. The invention including a processor base; an optics tube with a built-in light sources, a built-in video camera; a microphone, an auxiliary pedal and software.

13 Claims, 4 Drawing Sheets

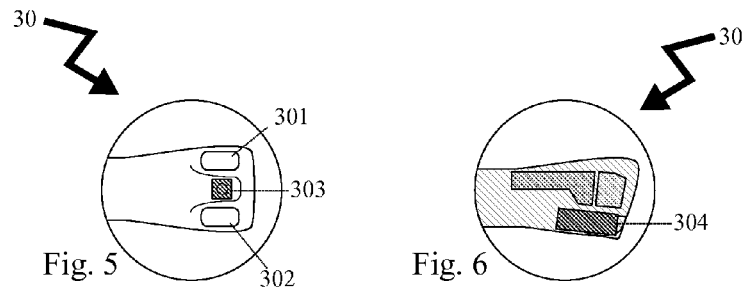
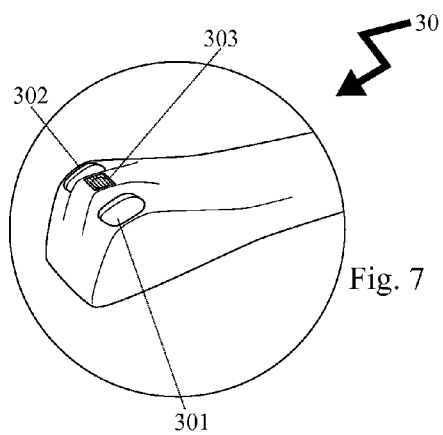
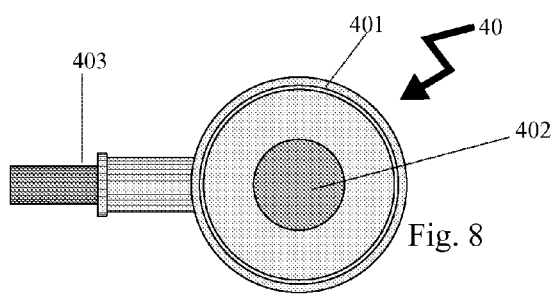
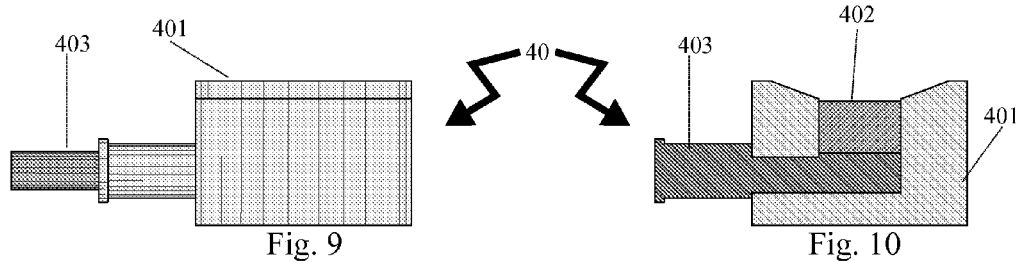

VIDEOLARYNGOSTROBOSCOPE

FIELD OF THE INVENTION

The present invention relates to medical devices and more particularly, to an innovative videolaryngostroboscope whose field of application includes otorhinolaryngology.

BACKGROUND OF THE INVENTION

It is known that human's vocal cords are located in the larynx. For that reason, the aim of laryngoscopy is to examine the general state of the vocal folds, detecting from a simple failure in the production of sounds to tumors and other serious anomalies. However, in many larynx examinations, an accurate visualization of the vocal folds function with the naked eye is impaired due to the depth to which this organ is located, as well as the high frequency vibration of these vocal folds when sounds are produced.

A variety of attempts have been made to perform this examination. One method has been to connect laryngoscopes to video cameras. However, due to the large size of these cameras, it was necessary to use a thin metal tube (called "optics tube"), with internal lenses that transmit image of the larynx to the camera's image sensor. These so-called video laryngoscopes, visualize the larynx by means of a camera, and display the final image upon a TV monitor.

However, in order for specialized physicians to assess accurately the general state of the vocal folds, is not simply enough to visualize the larynx, it is necessary to test the vocal cords. Asking the patient to produce sounds on several frequencies, while the physician observes the behavior of the vocal folds does this testing.

The human eye however, is not capable of capturing images at frequencies higher than 30 Hz (30 cycles per second). Above this frequency, the human eye loses its ability to observe one movement at a time, and it is impossible to perceive how the vocal cords work. This phenomenon is similar to the phenomena, which takes place when a party looks at the blades of a spinning fan. It is not possible to follow a single fan propeller blade separately. The velocity of the spinning of the blade causes the blade to appear as a single disk due to the human eye. This is because the rate at which the blade spins is significantly faster than the rate at which the human eye can perceive and process this information.

The solution to this problem was found to be the implementation and use of a second resource to the laryngoscopes, a stroboscopic light. Stroboscopy is a method of illumination where the light turns on and off at varying velocities (hundredth of seconds) providing frequency offset. This type of light is generally used in discotheques, which provides, for example, an intermittent aspect to the body movements. These apparent jumps between movements from one position to another solve the problem of the human eye not to see movements at high frequency. In the case of the use in discotheques, body movements look like "broken" because such movements are very slow for the use of such light source.

In the case of a stroboscopic illumination of a turned-on fan, for example, it is possible to follow a propeller blade rotating with very slow movements, when actually it is rotating at high speeds, which are invisible to the human eyes with a constant light. It was this application (to be able to see a movement in slow motion) that was adapted to the videolaryngoscopy.

As in the case of the cameras, the stroboscopic light source presents a large extreme size, which makes impossible to introduce it into the oral cavity of the patient. The solution found was the use of a fiber optic cable that directs the source light beam to the optics tube. In this way, it was possible to illuminate the larynx with a stroboscopic light source, transforming the high-frequency movements of the vocal cords in slow-motion movements, which makes possible to be accurately analyzed by physicians. This examination that started to use the stroboscopic light source is called "videolaryngostroboscopy".

Around the world, there is high incidence of larynx cancer. When detected at its early stage, the probability of cure of this type of cancer is increased to near 100%. The importance of the videolaryngostroboscopy lies in the fact that this is the single examination used in the diagnosis of this type of cancer.

The existing videolaryngostroboscopes available in the market use similar methods of image capture. Its functioning is based on the image capture of the larynx by means of an optics tube that is connected to a camera and a fiber optic cable, which allows it to illuminate and film the vocal folds.

If a common videolaryngostroboscope were separated in isolated items, we would have:

1. Video camera, generally a high resolution video camera;
2. Stroboscopic light source equipped internally with a xenon gas-filled lamp, which pulses at frequencies determined by the patient's voice or by the physician;
3. Optics tube: a metal tube generally made of stainless steel, with about 1 cm in diameter and 30 cm in length. It has the function of being inserted into the patient's oral cavity, providing illumination to the larynx and transferring the images captured by its internal lens to the camera's image sensor, at the other end;
4. Coupler: since the optics tube does not have a screw-type attachment system to be fastened to the camera, a coupler is nothing more than an adapter that attaches the optics tube to the camera;
5. Fiber optic cable: this cable directs luminous beams from the stroboscopic source to the optics tube, and;
6. Frequency sensor: a microphone used to capture the voice frequency of the patient.
7. Auxiliary pedal: during the examination, it allows the physician to control the speed of slow motion effect.

In this way, specialists who use traditional videolaryngostroboscopes in their performance area have to purchase each one of the above mentioned items separately, which are frequently made by international manufacturers, thereby incurring high costs to acquire each item and damages related to the warranty of these products.

Furthermore, traditional videolaryngostroboscopes, which utilize high cost items such as xenon gas-filled lamps and fiber optic cables, are typically high in cost and large in size. This causes to produce to be expensive and limits the portability of these items to various other locations. Consequently, it makes impossible the use of these items to provide medical assistance in diversified places such as streets, or remote locations, thus resulting in higher number of persons who cannot be treated by such a device.

In addition to these presented disadvantages, additional disadvantages that are present in devices that are currently in use include were also identified in by a meticulous analysis of traditional videolaryngostroboscope models, as follows:

It is uses xenon gas-filled lamp, which produces waves ranging from 6400K to 8000K and, consequently, color distortions are generated on the video monitor, resulting in a bluish image;

The light-emitting element is located at the external light source, which disturbs the professional who operates the apparatus, since easy-handling and practicality requirements are not being met by traditional videolaryngostroboscopes. Also, said light-emitting element has a lifetime of only 500 hours.

The camera is located external to the apparatus and connected to the optics tube by means of an adapter. So, it is necessary to purchase it separately, thus raising product prices.

Additionally, for this type of light-emitting element, it is necessary to use a light bulb, whose replacement is expensive, since it is an imported light bulb, and its price is in dollar.

The method for emitting light from the source to the optics tube is made via fiber-optic cable, thereby incurring high costs to acquire it, since it is sold separately.

Another adverse factor of traditional videolaryngostroboscopes is related to the fact that said optics tube has to be coated with stainless steel, which is a cold material and frequently causes nausea and discomfort to the patient, because it will be in contact with the patient's throat.

Besides other negative aspects that were identified, it is important to point out that:

Traditional videolaryngostroboscopes do not have an anti-fog system for the lens;

Traditional videolaryngostroboscopes do not have a coating for the optics tube, and;

As said traditional videolaryngostroboscopes are a combination of several pieces of equipment, their minimum weight is about 5000 g, which makes almost impossible to transport them and thus to provide care for out-patients.

Due to the fact that it uses the aforementioned functioning methods, traditional videolaryngostroboscope model incurs high production costs.

SUMMARY OF THE INVENTION

The present invention is a compact condensed, portable, videolaryngostroboscope that is able to provide otorhinolaryngology specialists with the possibility to examine accurately laryngeal inner cavities, visualizing voice disorders, following results after surgeries of tumors on the vocal cords and larynx, and registering video images. The videolaryngostroboscope of the present invention provides slow motion visualization and detailed analysis of the vocal cords movements, which are imperceptible to the naked eye due to its high frequency performance. The present invention allows a specialist to perform examinations of greater numbers of patients, aiming to assess the incidence of larynx cancer, thus facilitating its identification and thereby increasing the probability of cure.

The present videolaryngostroboscope is a compact, condensed, portable apparatus whose construction technique includes all elements necessary to the applicability and usability of the product, and there is no need to purchase components separately, as usual in the traditional market, which provides more accessible costs and practicality, since it is a light and easy-to-handle product. By purchasing a one-piece videolaryngostroboscope, the professional will have immediately all necessary functions for a perfect visualization of the vocal folds, in order to achieve accuracy on related examinations and similar procedures. Furthermore, the one-piece videolaryngostroboscope of the present invention can be easily transported to other places, thus allowing the professional to be able to provide care for outpatients in a variety of environments.

For these and other reasons, the present videolaryngostroboscope offers several advantages to the professional specialized in the otorhinolaryngology field. Therefore, it is a novel product in the market of similar products, which provides several benefits by its use.

The purpose of the foregoing Abstract is to enable the public, and especially the scientists, engineers, and practitioners in the art who are not familiar with patent or legal terms or phraseology, to determine quickly from a cursory inspection, the nature and essence of the technical disclosure of the application. The Abstract is neither intended to define the invention of the application, which is measured by the claims, nor is it intended to be limiting as to the scope of the invention in any way.

Still other features and advantages of the present invention will become readily apparent to those skilled in this art from the following detailed description describing preferred embodiments of the invention, simply by way of illustration of the best mode contemplated by carrying out my invention. As will be realized, the invention is capable of modification in various obvious respects all without departing from the invention. Accordingly, the drawings and description of the preferred embodiments are to be regarded as illustrative in nature, and not as restrictive in nature.

BRIEF DESCRIPTION OF THE DRAWINGS

Other features, objects and advantages of the present invention will become readily apparent and understood upon consideration of the following detailed description and attached drawings, wherein:

FIG. 5 illustrates a detailed view of the optics tube tip (30) of the videolaryngostroboscope, showing the LED 01 (301), LED 02 (302) and the lens of the image sensor (303), wherein all of them have a copper support;

FIG. 6 illustrates a detailed translucent view of the optics tube tip (30) of the videolaryngostroboscope, showing the image sensor (304) disposed internally;

FIG. 7 illustrates a detailed perspective view of the optics tube tip (30) of the videolaryngostroboscope;

FIG. 8 illustrates a superior view of the microphone (40) of the videolaryngostroboscope, showing its aluminum body (401), electret microphone (402) and cable (403);

FIG. 9 illustrates a lateral view of the microphone (40) of the videolaryngostroboscope;

FIG. 10 illustrates a lateral cross-section view of the microphone (40) of the videolaryngostroboscope, showing, internally, the electric microphone (402) and, externally, the aluminum body (401) and the cable (403);

DESCRIPTION OF THE PREFERRED EMBODIMENTS

Figure 1:
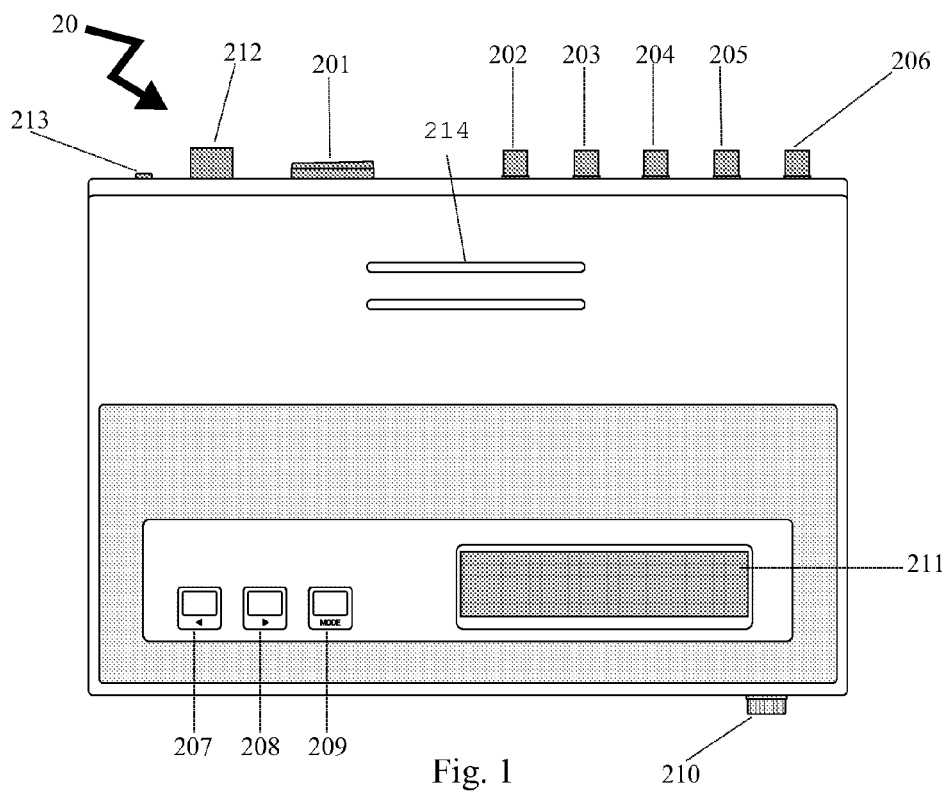
FIG. 1 illustrates a front view of the processor base (20) of the videolaryngostroboscope, according to the present invention, showing its construction technique, mainly the command buttons: power (201), auxiliary in (202), microphone in (203), pedal + (204), pedal − (205), video out (206), rewind (207), fast forward (208), mode (209), camera in (210); liquid crystal display (211); supports (214) of the optics tube (30) with on/off sensors; fuse button (212) and energy source button (213)
Figure 2:
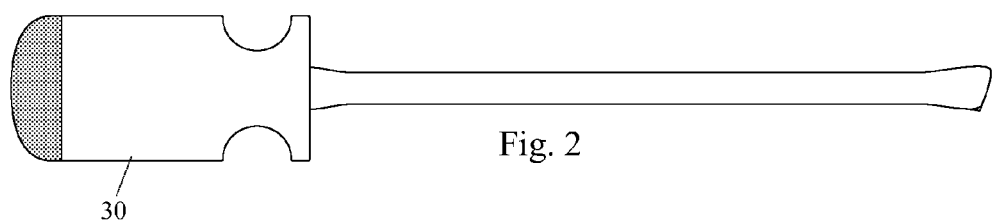
FIG. 2 illustrates a side view of the optics tube (30) of the videolaryngostroboscope.
Figure 3:
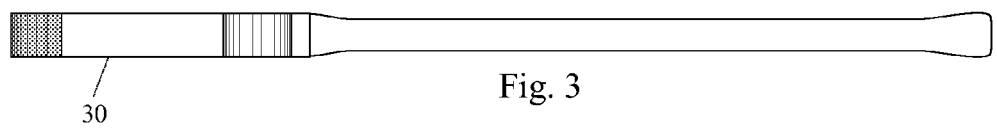
FIG. 3 illustrates an inferior view of the optics tube (30) of the videolaryngostroboscope.
Figure 4:
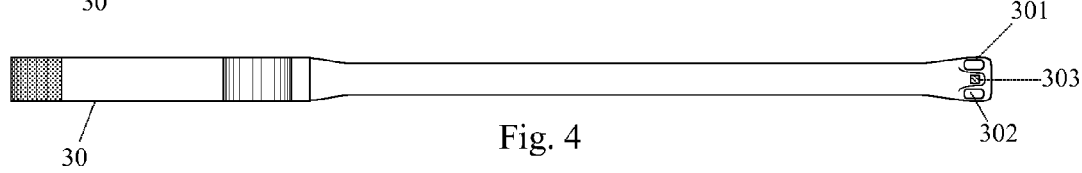
FIG. 4 illustrate a superior view of the optics tube (30) of the videolaryngostroboscope.
Figure 11:
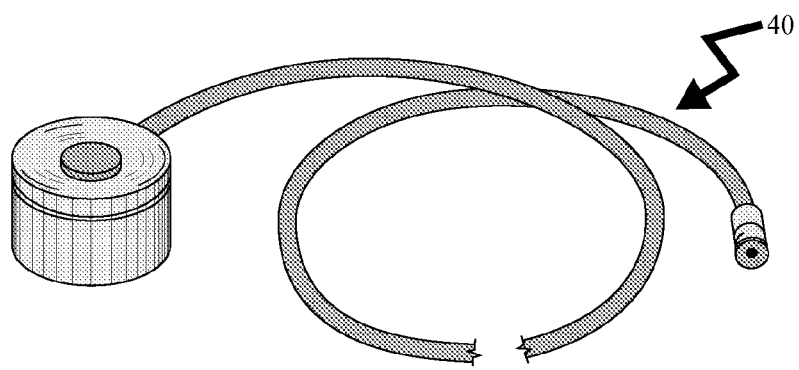
FIG. 11 illustrates a detailed view of the microphone (40) of the videolaryngostroboscope.
Figure 12:
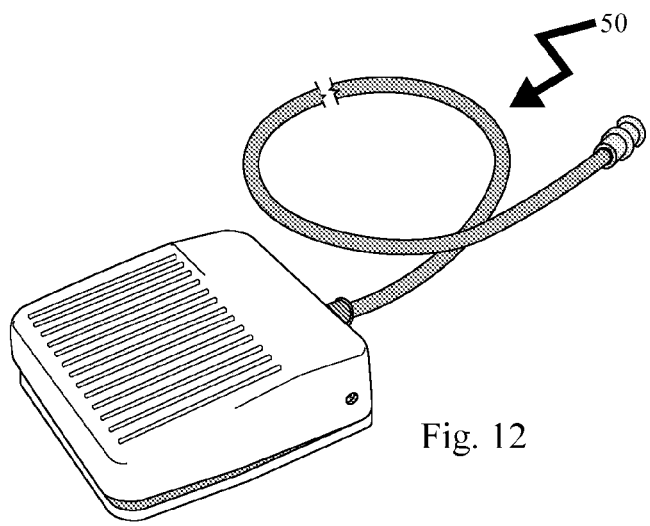
FIG. 12 illustrates a perspective view of the auxiliary pedal (50) of the videolaryngostroboscope.
Figure 13:
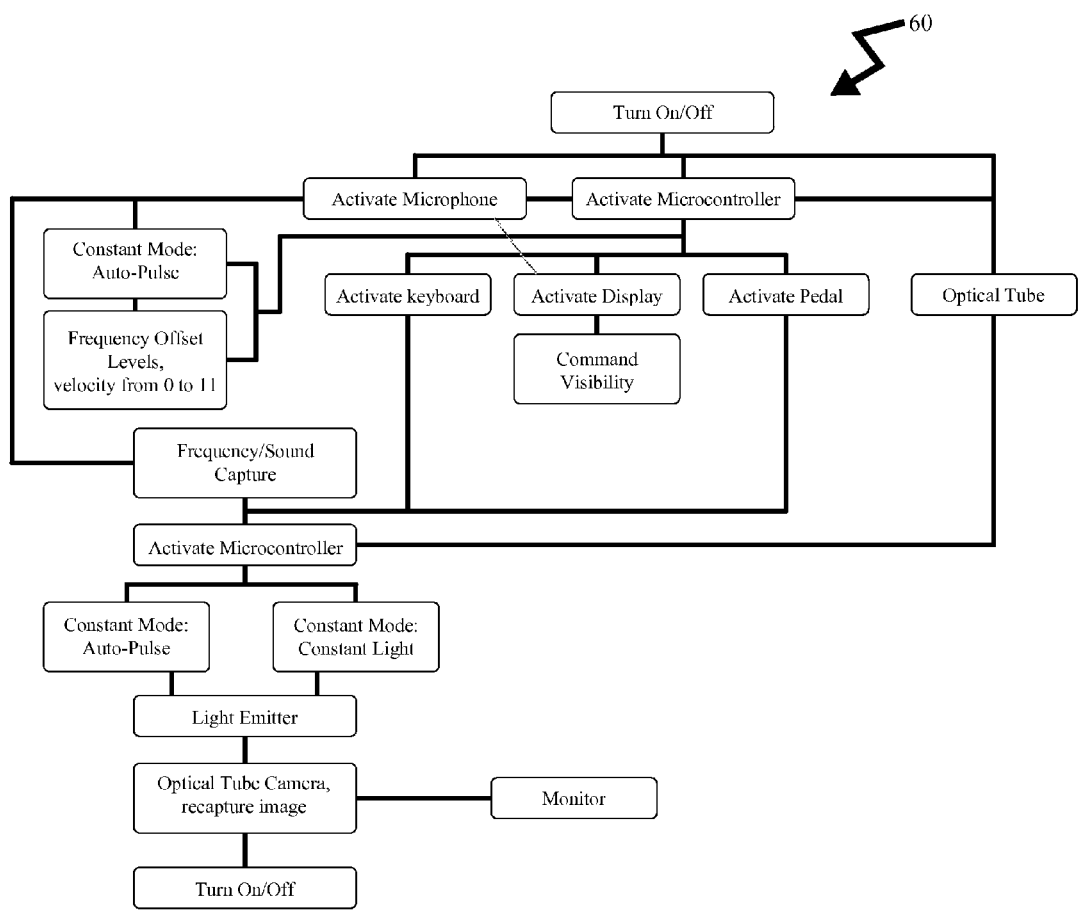
FIG. 13 shows a flowchart of the software (60) that will be responsible for all functionality of the videolaryngostroboscope.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

The present invention is a videolaryngostroboscope, and the following FIGS. 1-13 show various features and advantages of the present invention. Referring first now to FIG. 1, the present invention is made up of a processor base (20) that controls various peripherals including in the preferred embodiment the following:

1. Externally, the processor base (20) is provided with command buttons, a liquid crystal display (211), and connections to auxiliary equipment and peripherals. Said processor base is the "brain" of the apparatus, which manages the signal received by the microphone (40) and converts it into electric pulses to the stroboscopic light source. Internally, said processor base (20) is provided with a motherboard that manages all signals received by its peripherals, in which an application software (60) is responsible for all functionality of the videolaryngostroboscope.

2. The optics tube (30), is a piece that is inserted into the patient's oral cavity. In contrast of the traditional optics tube, the optics tube (30) of the videolaryngostroboscope, is equipped internally with LED's (301 and 302) and a CCD-type image sensor (303) that, together, they are responsible for illuminating and filming the larynx, respectively.

Moreover, said optics tube (30) of the videolaryngostroboscope, has an outer coating made of polyurethane plastic, by which the patient is isolated from direct contact with any type of metal. The advantage of this plastic coating is that it enables the patient to avoid thermal shock (metal "steals" heat), if said optics tube touches the patient's oral cavity walls. In addition to the comfort factor, said optics tube plastic coating prevents the occurrence of electric shocks that occasionally occur in some traditional optics tube, and avoids nausea and discomfort to the patient. Also, said optics tube of the videolaryngostroboscope, is in compliance with the requirements for impermeability and protection to internal apparatus components.

The optics tube (30) of the videolaryngostroboscope comprises a metallic structure made of internal aluminum; lens support made of copper; internal ¼" CCD image sensor; built-in 3 W white LED's; plastic finish with polyurethane paint.

The upper base and the lower base of said optics tube (30) comprise electric chips that receive all commands from said processor base (20), and they are responsible for all functions of said optics tube (30) related to the reception/transmission of images and feeding of light emitter.

The optics tube (30) comprises electric armored connector cables that transmits the signal to the video, feeds the light emitter, and a chamber.

3. The pedal (50) of the videolaryngostroboscope, is an extension of buttons (204 and 205) of the processor base (20). The pedal (50) allows the operator to control the apparatus even when said operator is distant from said processor base (20), holding said optics tube (30) and examining the patient.

4. The microphone (40) of the videolaryngostroboscope has the function of capturing sound signals emitted by the patient and transmit them to said processor base (20). In the base, said signal will reach the circuit that controls the stroboscopic light, and it will use said signal as a reference to emit a return signal to the light-emitting semiconductors.

The videolaryngostroboscope function consists of slow motion visualization of vocal folds movements by means of a video camera with stroboscopic illumination. Said slow motion visualization of these images is acquired with a light pulse at frequencies very close to the frequency of the emitted sound.

For example, if the patient emits a sound at a frequency of 200 Hz (200 cycles per second), his/her vocal cords are vibrating at this same frequency, that is, 200 Hz. In order to view the movement of the vocal cords in slow motion, it is necessary that the light pulse at a frequency of about 199.5 Hz. This difference of 0.5 Hz (half-cycle by second) is what will transform this movement into a slow motion movement.

Also, there is the possibility for the physician to view the same movement at a frequency of 200 Hz (200 cycles per second) as a frozen image on the screen. For this, it is just enough that the light also pulses at a frequency of 200 Hz (200 cycles per second). This, in turn, can be guided in two ways, as follows:

1. By the physician, who determines on the apparatus panel at which frequency the light has to pulse.

2. By the patient's voice frequency that, when captured by the microphone (40), transmits the values (in Hertz) that will be used as the reference to the light source. By using the microphone (40) of the videolaryngostroboscope, the patient will be free to emit sounds at random frequencies, since the light source will make the light to pulse at a frequency close to the captured frequency.

As it was analyzed, the videolaryngostroboscope, is responsible for the image capture and processing. However, in order to achieve a complete visualization of these images, it is necessary to connect a television monitor to the apparatus. In this way, the videolaryngostroboscope functioning is based on the following principles:

1. The sound emitted by the patient is captured by the microphone (40), converted into electric pulses and emitted to said processor base (20);

2. When electric pulses generated by the microphone (40) reach the processor base (20), they are directed to the circuit that controls the lighting system;

3. At the stroboscopic illumination control module, electric pulses are recognized and delayed in milliseconds;

4. After electric pulses are delayed, they go to the lighting system of the optics tube (30);

5. When electric pulses reach the two light-emitting diodes, they are converted into a white light and directed by a lens to the larynx;

6. Luminous rays shock against the larynx and they are reflected to the image sensor (303);

7. At the high-resolution image sensor (303), luminous rays are converted into electric pulses and directed to said processor base (20), which establishes automatically a connection to the video;

8. When the pulses emitted by said image sensor (303) reach said processor base (20), they go to the image control module;

9. At the video output, the signal goes directly to the high-resolution television monitor.

10. At the high-resolution television monitor, the NTSC video signal is finally converted into high-definition slow motion images.

The videolaryngostroboscope, comprises: processor base (20); optics tube (30) having built-in light source (301 and 302), built-in video camera (303 and 304); microphone (40), auxiliary pedal (50) and software (60).

In order to make said videolaryngostroboscope ready for use, a television monitor is the unique device that the user needs to acquire separately. But, on the contrary, in the case of traditional videolaryngostroboscopes, the customer must acquire all items separately and arrange them into a rack.

Due to the fact of having a camera (303) and the light source (304) connected to the optics tube (30), said videolaryngostroboscope, does not require the use of xenon gas-filled lamp and fiber optic cable, that is, the two main responsible for the for the increase in videolaryngostroboscope prices. Its alternative method of capture and illumination reduce its manufacturing costs, so, the videolaryngostroboscope of the present invention is cheaper than traditional videolaryngostroboscopes. Its costs are about 30 percent lower than traditional videolaryngostroboscopes, which makes the videolaryngostroboscope of the present invention an extremely accessible apparatus to physicians, for example, who until then practically cannot afford to purchase an analogous apparatus.

This improvement resulted in a portable apparatus that can be can be carried by medical field professionals and transported to any place, and thus to provide care for out-patients.

The color temperature of the light source of said improved videolaryngostroboscope, does not exceed 5,900 K; consequently, its quality of image transmission to the TV monitor is not deteriorated, that is, said improved videolaryngostroboscope provides true color visibility.

Said light-emitting element is in-built into the optics tube (30) end, and it is necessary to use two light bulbs, which are much cheaper than light bulbs used in traditional videolaryngostroboscopes.

In relation to their lifetime, said light bulbs have a lifetime of more than 3,000 hours of use, and their lifetime can reach 50,000 hours of use, depending on how is the process of use thereof. Consequently, there is a decrease in the product costs in relation to the traditional videolaryngostroboscope, since the later uses only one light bulb, but with higher prices and a lifetime of only 500 hours.

Since the videolaryngostroboscope, is compact, there is no need to include a fiber optic cable to transmit light from the light source to the optics tube; consequently, the product costs are reduced.

The videolaryngostroboscope of the present invention also comprises an anti-fog system for said lens and a coating made of polyurethane plastic.

Since the videolaryngostroboscope of the present invention has a camera in built into said optics tube (30), there is no risk of damage to the camera.

Also, since the videolaryngostroboscope of the present invention is compacted into one-piece, its weight is only 500 g, that is, it is an easy-handle, easy-moving, and light product.

Therefore, the present invention relates to an improvement that, in function of the apparatus technological arrangement, it resulted in a product that provides several benefits by its use, revolutionizing otorhinolaryngology specialists who will use a novel product that will replace successfully traditional videolaryngostroboscopes, since it provides the following benefits: lower costs, maintenance and warranty advantages; it is an easy-to-transport, easy-to-handle product; it is a portable, compact light apparatus; it uses all the necessary technology for use; it comprises advanced technologically components, which results in operations with more quality and efficiency; its lifetime is longer than traditional videolaryngostroboscopes, among other advantageous aspects.

While there is shown and described the present preferred embodiment of the invention, it is to be distinctly understood that this invention is not limited thereto, but may be variously embodied to practice within the scope of the following claims. From the foregoing description, it will be apparent that various changes may be made without departing from the spirit and scope of the invention as defined by the following claims.

What is claimed is:

1. A Videolaryngostroboscope that allows a physician to accurately examine a patient's laryngeal inner cavities, visualize voice disorders, follow results after surgeries of tumors on the vocal cords and larynx, and register video images, utilizing a video camera with stroboscopic illumination, wherein said visualization is acquired with a light pulse at frequencies very close to the frequency of an emitted sound, said Videolaryngostroboscope comprising:

a processor base for controlling a plurality of peripherals, wherein said processor base comprises a plurality of external command buttons, said buttons comprising a power button, an auxiliary in button, a microphone in button, a pedal + button, a pedal − button, a video out button, a rewind button, a fast forward button, a mode button, and a camera in button, said processor base further comprising a liquid crystal display, supports of an optics tube with on/off sensor, a fuse button, and an energy source button;

the optics tube configured for insertion into a patient's oral cavity, said optics tube further comprising a stroboscopic light source;

a microphone for receiving a signal;

a pedal; and software for managing said microphone signal, converting said microphone signal into electric pulses to the stroboscopic light source, and managing signals received by said peripherals.

2. The Videolaryngostroboscope of claim 1 wherein said optics tube further comprises an image sensor lens, and a CCD-type image sensor, and wherein said stroboscopic light source comprises LEDs.

3. The Videolaryngostroboscope of claim 2, wherein said optics tube has an outer coating made of polyurethane plastic.

4. The Videolaryngostroboscope of claim 2, wherein said optics tube has a metallic structure made of aluminum and a lens support made of copper, wherein said CCD-type image sensor is an internal ¼" CCD image sensor, and wherein said LEDs are built-in 3 W white LEDs.

5. The Videolaryngostroboscope of claim 2, wherein said optics tube comprises an upper base and a lower base, wherein said upper base and said lower base of said optics tube each comprise electric chips that receive commands from said processor base, transmit images to said processor base, and feed information to said stroboscopic light source.

6. The Videolaryngostroboscope, according to claim 1, wherein said microphone captures sound signals emitted by the patient and transmits them to said processor base.

7. The Videolaryngostroboscope of claim 1 further wherein said pedal is an extension of the pedal + and pedal − buttons of the processor base, wherein said pedal allows said physician to control the apparatus even when said physician is distant from the processor base, holding the optics tube and examining the patient.

8. The Videolaryngostroboscope of claim 1, wherein color temperature of the light source does not exceed 5,900 K.

9. The Videolaryngostroboscope of claim 1, wherein the Videolaryngostroboscope includes light bulbs.

10. The Videolaryngostroboscope of claim 1 further, wherein said optics tube further comprises an internal lens having an anti-fog system.

11. The Videolaryngostroboscope of claim 1 further comprising a camera in built into said optics tube.

12. The Videolaryngostroboscope of claim 1 further comprising electric armored connector cables.

13. A Videolaryngostroboscope that allows a physician to accurately examine a patient's laryngeal inner cavities, said Videolaryngostroboscope comprising:
- a processor base for controlling a plurality of peripherals, wherein said processor base comprising:
  - a plurality of external command buttons, said buttons comprising a power button, an auxiliary in button, a microphone in button, a pedal button, a pedal – button, a video out button, a rewind button, a fast forward button, a mode button, and a camera in button,
  - a liquid crystal display,
  - supports of the optics tube with on/off sensors,
  - a fuse button, and
  - an energy source button;
- an optics tube configured for insertion into a patient's oral cavity, said optics tube comprising:
  - a metallic structure made of aluminum,
  - a lens support made of copper,
  - an outer coating made of polyurethane plastic,
  - a stroboscopic light source; wherein color temperature of said light source does not exceed 5,900 K, wherein said stroboscopic light source comprises 3 W white LEDs,
  - an image sensor lens having an anti-fog system,
  - an internal ¼" CCD image sensor,
  - an upper base and a lower base, wherein said upper base and said lower base of said optics tube each comprise electric chips that receive commands from said processor base, transmit images to said processor base, and feed information to said stroboscopic light source, and
  - a camera;
- a microphone for receiving sound signals emitted by the patient and transmits them to said processor base;
- a pedal, wherein said pedal is an extension of the pedal and pedal – buttons of the processor base, wherein said pedal allows said physician to control the apparatus even when said physician is distant from the processor base, holding the optics tube and examining the patient;
- electric armored connector cables; and
- software for managing said microphone signal, converting said microphone signal into electric pulses to the stroboscopic light source, and managing signals received by said peripherals.

\* \* \* \* \*

UNITED STATES PATENT AND TRADEMARK OFFICE
CERTIFICATE OF CORRECTION

PATENT NO.        : 7,654,952 B2                                           Page 1 of 1
APPLICATION NO.   : 11/382613
DATED             : February 2, 2010
INVENTOR(S)       : Ciro Timoteo Ott It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 659 days.

Signed and Sealed this

Twenty-third Day of November, 2010

David J. Kappos
*Director of the United States Patent and Trademark Office*